United States Patent
Tani

(10) Patent No.: US 6,884,442 B2
(45) Date of Patent: Apr. 26, 2005

(54) ANTI-INFLAMMATORY AGENT AND FOODS AND DRINKS CONTAINING THE SAME

(75) Inventor: Michio Tani, Wanchai (HK)

(73) Assignee: Herb Road Company, Wanchai (HK)

( * ) Notice: Subject to any disclaimer, the term of this patent is extended or adjusted under 35 U.S.C. 154(b) by 109 days.

(21) Appl. No.: 10/279,971

(22) Filed: Oct. 25, 2002

(65) Prior Publication Data

US 2003/0082246 A1 May 1, 2003

Related U.S. Application Data

(63) Continuation-in-part of application No. 10/198,990, filed on Jul. 22, 2002.

(30) Foreign Application Priority Data

Oct. 26, 2001 (JP) ......................................... 2001-329049
Aug. 26, 2002 (JP) ......................................... 2002-244913

(51) Int. Cl.[7] ............................................... A61K 35/78
(52) U.S. Cl. ........................ 424/745; 424/725; 424/765; 424/776; 424/774
(58) Field of Search ................................. 424/725, 745, 424/765, 776, 774

(56) References Cited

U.S. PATENT DOCUMENTS 5,916,565 A * 6/1999 Rose et al.

FOREIGN PATENT DOCUMENTS

| JP | 61-291524 | 12/1986 |
|---|---|---|
| JP | 1-121217 | 5/1989 |
| JP | 7-215884 | 8/1995 |
| JP | 11-318387 | * 11/1999 |

OTHER PUBLICATIONS

Castleman (The Healing Herbs, (1991), Rodale Press, Pennsylvania, pp. 169–172 and 225–228).* www–ang.kfunigraz.ac.at/~katzer/engl/Peri_fru.html.*

* cited by examiner

Primary Examiner—Susan D. Coe
(74) Attorney, Agent, or Firm—Young & Thompson

(57) ABSTRACT

An anti-inflammatory agent exhibiting an anti-inflammatory function is provided, which includes either a set of dried substances or an extract of *Perilla* leaf, *Cacao* and Fennel, and preferably *Perilla* leaf, *Cacao*, Fennel, Fenugreek seed, Rosemary, *Juniper* berry and Celery seed. This specific set or combination of those natural herbs is effective to relax and suppress symptoms of allergy, particularly holistic symptoms of allergic rhinitis, without causing any substantive adverse effects. Since all of the ingredients included in agent are derived from the natural herbs, a long-term administration of the agent may cause substantively no adverse effects. Also, inclusion of the agent into foods and drinks is also useful.

5 Claims, No Drawings

ANTI-INFLAMMATORY AGENT AND FOODS AND DRINKS CONTAINING THE SAME

This application is a continuation-in-part of co-pending application No. 10/198,990, filed on Jul. 22, 2002, the entire contents of which are hereby incorporated by reference.

BACKGROUND OF THE INVENTION

1. Field of the Invention

The present invention relates to an anti-inflammatory agent and fools and drinks containing the agent, and more particularly to an anti-inflammatory agent effectively inhibiting allergic diseases such as pollen disease and highly suppressing adverse reactions as compared to drugs particularly in case of long-term administration as well as to fools and drinks containing the agent.

2. Description of the Related Art

The pollen disease is one of various allergic diseases such as allergic rhinitis. In Japan, the pollen disease has frequently appeared but mostly in the last two decades. In recent years, the incidence rate of the pollen disease has been on the remarkable increase. At present, approximately 30% of the nation of Japan has displayed any allergic symptoms caused by the pollen disease.

In the past, a typical example of allergy-causing pollens was only a pollen of cryptomeria. In contrast, recently there have often appeared various allergic symptoms due to not only the pollen of cryptomeria but also other pollens, for example, of cypress and ragweed. Such a variety of allergy-causing pollens results in an increased term for possible incidences of the pollen diseases. Further, other cases of allergic symptoms caused by house dusts or mites have been affirmed. In these cases, such allergic symptoms may often be continued throughout the year.

Research of the therapy for the pollen diseases has widely and aggressively been made, and some available measures of therapy have already been developed and used in clinical therapy. Notwithstanding, these therapy measures have not yet demonstrated the desired almost perfect and satisfactory effects and results of therapy due to those merits and demerits. Incidence of the pollen diseases causes various unpleasant symptoms such as sneeze, rhinitis, rhinorrhea, rhinophyma, headache and heavy itch on eyes. Administration of therapeutic drug for reducing and suppressing such unpleasant symptoms may, unfortunately, however, cause undesired adverse effects such as sleepiness. Either the various unpleasant symptoms or the undesired adverse effects would be influential to the quality of life to no small extent.

In the meantime, artificially-prepared anti-allergic and steroid drugs have already been developed and used for clinical therapy. A long-term administration of those drugs may, however, cause various deteriorations of symptom such as rebound phenomenon and undesired adverse effects such as abnormal sleepiness due to those strong activation to central nervous system of human, and undesirable influences to endocrine system of human. In all cases, the administration of those drugs should be made according to the instructions of medical doctor.

In parallel to the research and developments of the artificially-prepared drugs, it was also attempted to find out any natural anti-allergic substances obtainable from natural foods because natural anti-allergic substances may be safe for human body and almost free from any substantive adverse effects. Developments of foods containing those natural anti-allergic substances are disclosed in three Japanese laid-open patent publications No. 61-291524, No. 1-121217, and No. 7-215884. Typical examples of well known natural anti-allergic substances are *Rubussuavzssimus* extract and *Perilla frutescens* leaf extract. *Rubussuavissimus* extract is extracted by a hot water from leaf of *Rubussuavissimus*. *Perilla frutescens* leaf extract is extracted by a hot water from leaf of *Perilla frutescens*.

As results of the clinical researches for those extracts, it was confirmed that Rubussuavissimus extract is effective to relax allergic symptoms and suppress allergic incidences onto circulatory organs such as rhinitis, sneeze and soreness on throat, while *Perilla frutescens* leaf extract is effective to relax and suppress skin inflammation.

Further, those natural food materials would be extremely safe to human body upon a long-term intake and be almost free from any substantive adverse effects because those natural food materials have been taken in the past long-term. Those natural anti-allergic substances have been utilized as anti-allergy functional ingredient for the anti-allergic foods.

In conclusion, as described above, the artificially-prepared anti-allergic drugs may cause various adverse effects, and thus should be administrated in accordance with the medical doctor's instructions. Since the long-term administration of those drugs should be avoided, those drugs would thus be unsuitable for relaxation and suppression of the allergic symptoms for the long-term.

The above-described natural anti-allergic substances obtainable from the foods are superior in safety to the human body in case of the long-term intake and also are almost free of any substantive adverse effects. Notwithstanding, these natural anti-allergic substances suppress only part of vital allergic reactions which will give rise to the allergic disease. Namely, the natural anti-allergic substances are effective for relaxation and suppression of part of the allergic symptoms, but not for holistic symptoms.

In the above circumstances, a novel anti-inflammatory agent and fools and drinks containing the agent free from the above problems are desirable.

SUMMARY OF THE INVENTION

Accordingly, it is an object of the present invention to provide a novel anti-inflammatory agent free from the above problems.

It is a further object of the present invention to provide a novel anti-inflammatory agent exhibiting superior anti-inflammatory effects.

It is a still further object of the present invention to provide a novel anti-inflammatory agent effective to relax and suppers symptoms of allergy, particularly holistic symptoms of allergic rhinitis.

It is yet a further object of the present invention to provide a novel anti-inflammatory agent free from any substantive adverse effects.

It is yet a further object of the present invention to provide a novel anti-inflammatory agent with high safety to human body in a long-term administration.

In addition, also it is an object of the present invention to provide foods and drinks containing a novel anti-inflammatory agent free from the above problems.

It is a further additional object of the present invention to provide foods and drinks containing a novel anti-inflammatory agent exhibiting superior anti-inflammatory effects.

It is a still further additional object of the present invention to provide foods and drinks containing a novel anti-inflammatory agent effective to relax and suppers symptoms of allergy, particularly holistic symptoms of allergic rhinitis.

It is yet a further additional object of the present invention to provide foods and drinks containing a novel anti-inflammatory agent free from any substantive adverse effects.

It is still more additional object of the present invention to provide foods and drinks containing a novel anti-inflammatory agent with high safety to human body in a long-term administration.

The present invention was made and the above objects were achieved based on a long-term experiment in the oriental medicine of the present inventor for thirty five years.

An anti-inflammatory agent exhibiting an anti-inflammatory function is provided, which includes either a set of dried substances or an extract of *Perilla* leaf, *Cacao* and Fennel, and preferably *Perilla* leaf, *Cacao*, Fennel, Fenugreek seed, Rosemary, *Juniper* berry and Celery seed. This specific set or combination of those natural herbs is important and essential for the present invention to provide desired superior anti-inflammatory effects, for example, to relax and suppress symptoms of allergy, particularly holistic symptoms of allergic rhinitis, without causing any substantive adverse effects. Since all of the ingredients included in the anti-inflammatory agent are derived from the natural herbs which are highly safe to human body, a long-term administration of the anti-inflammatory agent may cause substantively no adverse effects. Also, foods and drinks containing the anti-inflammatory agent are also provided.

The above and other objects, features and advantages of the present invention will be apparent from the following descriptions.

DETAILED DESCRIPTION OF THE PREFERRED EMBODIMENTS

A primary aspect of the present invention is to provide an anti-inflammatory agent exhibiting an anti-inflammatory function, wherein the anti-inflammatory agent includes a set of dried substances of *Perilla* leaf, *Cacao* and Fennel, and preferably *Perilla* leaf, *Cacao*, Fennel, Fenugreek seed, Rosemary, *Juniper* berry and Celery seed. This specific set or combination of those natural herbs is important and essential for the present invention to provide desired superior anti-inflammatory effects, for example, to relax and suppress symptoms of allergy, particularly holistic symptoms of allergic rhinitis, without causing any substantive adverse effects. Since all of the ingredients included in the anti-inflammatory agent are derived from the natural herbs which are highly safe to human body, a long-term administration of the anti-inflammatory agent may cause substantively no adverse effects.

The anti-inflammatory agent may practically be prepared by blending or mixing those herbs in particular conditions that respective ranges of relative ratios in weight of the dried substances of *Perilla* leaf, *Cacao* and Fennel are 6~2:6~2:4~1. In the practical preparation for the agent, typically, those respective relative ratios in weight of the dried substances of *Perilla* leaf, *Cacao* and Fennel may be 3:3:2.

The anti-inflammatory agent may practically be prepared by blending or mixing those herbs in particular conditions that respective ranges of relative ratios in weight of the dried substances of *Perilla* leaf, *Cacao*, Fennel, Fenugreek seed, Rosemary, *Juniper* berry and Celery seed are 6~2:6~2:4~1:4~1:4~1:3~0.3. In the practical preparation for the agent, typically, those respective relative ratios in weight of the dried substances of *Perilla* leaf, *Cacao*, Fennel, Fenugreek seed, Rosemary, *Juniper* berry and Celery seed may be 3:3:2:2:2:2:1.

In the practical preparation for the agent, the dried substances may preferably and conveniently be in the form of mixed dry powders.

Optionally, it may be possible to add a sweetness-providing natural herb, for example, Stevia to the above anti-inflammatory agent, wherein respective ranges of relative ratios in weight of *Perilla* leaf, *Cacao*, Fennel, Fenugreek seed, Rosemary, *Juniper* berry, Celery seed and Stevia are 6~2:6~2:4~1:4~1:4~1:4~1:3~0.3:3~0.3.

In the practical administration of the agent, an appropriate dose depends on the state of disease, and patient's age and other factors. One typical example of the daily dose may be in the range of 15–25 g.

Another primary aspect of the present invention is to provide an anti-inflammatory agent exhibiting an anti-inflammatory function, wherein the anti-inflammatory agent includes an extract extracted from *Perilla* leaf, *Cacao*, Fennel, Fenugreek seed, Rosemary, *Juniper* berry and Celery seed. This specific set or combination of those natural herbs is important and essential for the present invention to provide desired superior anti-inflammatory effects, for example, to relax and suppress symptoms of allergy, particularly holistic symptoms of allergic rhinitis, without causing any substantive adverse effects. Since all of the ingredients included in the anti-inflammatory agent are derived from the natural herbs which are highly safe to human body, a long-term administration of the anti-inflammatory agent may cause substantively no adverse effects.

In the practical preparation, the above specific extract may be extracted by a hot water from a set of dried substances of *Perilla* leaf, *Cacao*, Fennel, Fenugreek seed, Rosemary, *Juniper* berry and Celery seed. Those dried substances may be obtained by either directly drying those herbs in the original or crude shape, or in combination of subsequent grinding the dried herbs into dry powders. The practical extraction may, typically, be made by using a hot water of a temperature in the range of 90–100° C. and for a time in the range of 30–50 minutes. A weight ratio of the hot water with reference to the set of dried substances of those herbs may be, but not limited to, in the range of 10–100 times, and preferably 15–25 in the extraction-operation and efficiency points of view.

The above extract included in the agent may be either in a dry-state and a liquid state. The dry-state extract may practically be obtained by drying the liquid state-extract extracted by the hot water. The available dry processes are, for example, spray-dry and freeze-dry to form a granular extract.

Similarly to the first primary aspect, it may optionally be possible to add Stevia as a natural herb sweetener to the agent.

In the practical administration of the agent, an appropriate dose depends on the state of disease, and patient's age and other factors. One typical example of the daily dose may be in the range of, but not limited to, 15–25 g.

Still another aspect of the present invention is to provide food and drink including an effective ingredient which comprises the novel anti-inflammatory agent described above in connection with the first primary and second primary aspects of the present invention. One typical example of the practical amount of the effective ingredient included in food and drink may be in the range of, but not limited to, 1–20 percents by weight.

Applicable foods and drinks are any foods and drinks which may include, but not limited to, general foods and drinks, health foods and drinks, and nutritionally supplemental foods and drinks. Typical examples of the general foods and drinks may include various soups, various beverages such as juices, liquors, mineral waters, coffees and teas, various confectioneries such as gum, candy, chocolate, snack and jelly, and various noodles such as buckwheat noodle, Japanese wheat noodle, Chinese wheat noodle, and pasta Intake of those foods and drinks in the daily diets is effective for prevention and relaxation of the allergic symptoms in the long-term without causing any substantive adverse effect. The very long-term intake of those foods and drinks in the daily diets may ameliorate allergic predisposition.

In Japanese laid-open patent publication No. 9-87189 which is hereby incorporated as reference, it is disclosed that extracts from *Labiatae* plant such as leaf, flower and root thereof have anti-allergic functions.

In contrast, the present inventor discovered that the above-described specific set or combination of the natural herbs is important and essential to provide desired superior anti-inflammatory effects, for example, to relax and suppress symptoms of allergy, particularly holistic symptoms of allergic rhinitis, without causing any substantive adverse effects. Since all of the ingredients included in the anti-inflammatory agent are derived from the natural herbs which are highly safe to human body, a long-term administration of the anti-inflammatory agent may cause substantively no adverse effects.

The following examples are typical examples for practicing the foregoing aspects of the present invention. Although the subject matters of the present invention have been described in details, the following additional descriptions in one or more typical preferred embodiments or examples will be made for making it easy to understand the typical modes for practicing the foregoing aspects of the present invention.

EXAMPLE 1

Preparation of Anti-inflammatory Agent

In one preferred example of the present invention, an anti-inflammatory agent was prepared by blending dry powers of the dry herbs at specific weight ratios as follows.

3 g of *Perilla* leaf, 3 g of *Cacao*, 2 g of Fennel, 2 g of Fenugreek seed, 2 g of Rosemary, 2 g of *Juniper* berry, 1 g of Celery seed and 0.7 g of Stevia were mixed in dry-powered state to prepare the anti-inflammatory agent. This anti-inflammatory agent will be refereed to as the anti-inflammatory agent of example 1 of the present invention.

EXAMPLE 2

Preparation of Anti-inflammatory Agent

In one preferred example of the present invention, an anti-inflammatory agent was prepared by blending dry powers of the dry herbs at specific weight ratios as follows.

3 g of *Perilla* leaf, 3 g of *Cacao* and 2 g of Fennel were mixed in dry-powered state to prepare the anti-inflammatory agent. This anti-inflammatory agent will be refereed to as the anti-inflammatory agent of example 2 of the present invention.

COMPARATIVE EXAMPLE 1

Preparation of Anti-inflammatory Agent

In one comparative-example of the prior art, an anti-inflammatory agent was prepared by blending dry powers of the dry herbs at specific weight ratios as follows.

3 g of *Perilla* leaf and 2 g of Rosemary were mixed in dry-powered state to prepare the anti-inflammatory agent. This anti-inflammatory agent will be refereed to as the anti-inflammatory agent of comparative example 1.

COMPARATIVE EXAMPLE 2

Preparation of Anti-inflammatory Agent

In another comparative-example of the prior art, an anti-inflammatory agent was prepared by blending dry powers of the dry herbs at specific weight ratios as follows.

3 g of *Cacao* and 2 g of Fennel were mixed in dry-powered state to prepare the anti-inflammatory agent. This anti-inflammatory agent will be refereed to as the anti-inflammatory agent of comparative example 2.

Clinical Test and Evaluation 37-patients of cryptomeria pollen disease with sneeze and rhinitis symptoms seasonally appeared in February through May and/or other allergic diseases continuously appeared throughout the year were treated as follows.

A first group of 31 cases of the 42-patients administrated daily two times an extract which was extracted by a hot water of 100° C. for 35 minutes from the anti-inflammatory agent of example 1 of the present invention.

A second group of 5 cases of the 42-patients administrated daily two times an extract which was extracted by a hot water of 100° C. for 35 minutes from the anti-inflammatory agent of example 2 of the present invention.

A third group of other 3 cases administrated daily two times an extract which was extracted by a hot water of 100° C. for 35 minutes from the anti-inflammatory agent of comparative example 1.

A fourth group of the remaining 3 cases administrated daily two times an extract which was extracted by a hot water of 100° C. for 35 minutes from the anti-inflammatory agent of comparative example 2.

The above administrations were continued for four weeks and then the evaluations were made on the basis of the following criterions.

"A": Remarkably effective: all of the symptoms were disappeared

"B": Effective: most of the symptoms were disappeared, but a few symptoms sill resided "C": Somewhat effective: only a,few symptoms were disappeared but most of the symptoms sill resided "D": Not effective none: of any significant effect was confirmed.

The results of the evaluations are shown on the following Table 1.

TABLE 1

| | criterions | | | |
|---|---|---|---|---|
| | "A" | "B" | "C" | "D" |
| first group | 14 cases | 9 cases | 5 cases | 3 cases |
| second group | 2 cases | 1 case | 0 case | 0 case |
| third group | 0 case | 0 case | 1 case | 2 cases |
| fourth group | 0 case | 0 case | 0 case | 3 cases |

From the first group, it was demonstrated that administration of the anti-inflammatory agent of example 1 of the present invention is, in most cases, significantly effective to relax and suppress the cryptomeria pollen symptoms and other permanent allergic symptoms. In addition, it was also confirmed that all of the 31 cases of the first group were free from any adverse effects. A certain amelioration in the cryptomeria pollen symptoms and other permanent allergic symptoms was initiated on third day from the start of the administration. One week after the start of administration, most of the 31 cases of the first group subjectively felt a certain reduction in cryptomeria pollen symptoms and other permanent allergic symptoms. Two weeks after the start of administration, the above remarkable effectiveness to relax and suppress the cryptomeria pollen symptoms and other permanent allergic symptoms was confirmed.

In addition, from the second group, it was demonstrated that administration of the anti-inflammatory agent of example 1 of the present invention is, some cases, significantly effective to relax and suppress the cryptomeria pollen symptoms and other permanent allergic symptoms. It was also confirmed that all of the 5 cases of the first group were free from any adverse effects. A certain amelioration in the cryptomeria pollen symptoms and other permanent allergic symptoms was initiated on third day from the start of the administration. One week after the start of administration, a majority of the 5 cases of the second group subjectively felt a certain reduction in cryptomeria pollen symptoms and other permanent allergic symptoms. Two weeks after the start of administration, the above remarkable effectiveness to relax and suppress the cryptomeria pollen symptoms and other permanent allergic symptoms was confirmed.

In contrast, the third and fourth groups demonstrated that either administration of the anti-inflammatory agents of comparative examples 1 and 2 is not substantially effective to relax and suppress the cryptomeria pollen symptoms and other permanent allergic symptoms.

In conclusion, the above text demonstrated that the above-described specific set or combination of the natural herbs is important and essential to provide desired superior anti-inflammatory effects, for example, to relax and suppress symptoms of allergy, particularly holistic symptoms of allergic rhinitis, without causing any substantive adverse effects.

EXAMPLE 2

Preparation of Soup

In another preferred example of the present invention, a soup containing the above-described anti-inflammatory agent of example 1 of the present invention was prepared, wherein the ingredients of the soup were 20 wt-% of the anti-inflammatory agent, 30 wt-% of green gram, 1.5 wt % of Stevia, 1 wt-% of salt and 47.5 wt-% of water.

From this example, it was demonstrated that inclusion of the anti-inflammatory agent into the foods and drinks, which may be taken by daily diets, is practically useful for habitual intake of the anti-inflammatory agent for a long-term, for example, throughout the year in order to previously prevent allergic disease and ameliorate allergic predisposition.

Although the invention has been described above in connection with several preferred embodiments therefor, it will be appreciated that those embodiments have been provided solely for illustrating the invention, and not in a limiting sense. Numerous modifications and substitutions of equivalent materials and techniques will be readily apparent to those skilled in the art after reading the present application, and all such modifications and substitutions are expressly understood to fall within the true scope and spirit of the appended claims.

What is claimed is:

1. Anti-inflammatory agent consisting of extracts of *Perilla* leaf, *Cacao* and Fennel.

2. An anti-inflammatory agent consisting of extracts of *Perilla* leaf, *Cacao*, Fennel, Fenugreek seed, Rosemary, *Juniper* berry and Celery seed.

3. The agent as claimed in claim 1, wherein respective relative ratios in weight of said extracts of *Perilla* leaf, *Cacao* and Fennel are 3:3:2.

4. The agent as claimed in claim 2, wherein respective relative ratios in weight of said extracts of *Perilla* leaf, *Cacao*, Fennel, Fenugreek seed, Rosemary, *Juniper* berry and Celery seed are 3:3:2:2:2:2:1.

5. Food and drink as claimed in claim 2, wherein respective ranges of relative ratios in weight of said extracts of *Perilla* leaf, *Cacao*, Fennel, Fenugreek seed, Rosemary, *Juniper* berry and Celery seed are 6~2:6~2:4~1:4~1:4~1:4~1:3~0.3.

* * * * *